United States Patent
Chen et al.

(10) Patent No.: US 8,080,140 B2
(45) Date of Patent: Dec. 20, 2011

(54) PROCESS FOR DEBOTTLENECKING A SYSTEM FOR THE SEPARATION OF A CONJUGATED DIOLEFIN

(75) Inventors: May-Ru Chen, Baton Rouge, LA (US); Micheal E. Smith, Denham Springs, LA (US); Ross T. Garner, Denham Springs, LA (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 1280 days.

(21) Appl. No.: 11/787,996

(22) Filed: Apr. 18, 2007

(65) Prior Publication Data

US 2008/0257711 A1    Oct. 23, 2008

(51) Int. Cl.
  *B01D 3/06*  (2006.01)
  *B01D 3/34*  (2006.01)
  *B01D 3/00*  (2006.01)

(52) U.S. Cl. ............... 203/88; 203/50; 203/57; 203/59; 203/71; 203/8

(58) Field of Classification Search .................... 203/50, 203/59, 73, 80, 88, DIG. 19, DIG. 25, 9, 203/71; 585/615, 860, 810; 208/352, 361
See application file for complete search history.

(56) References Cited

U.S. PATENT DOCUMENTS

| | | | |
|---|---|---|---|
| 2,371,817 A * | 3/1945 | Frey | 585/835 |
| 3,167,501 A | 1/1965 | Woodle | |
| 3,377,267 A * | 4/1968 | Spars | 208/108 |
| 3,436,346 A | 4/1969 | Takao et al. | |
| 3,436,438 A * | 4/1969 | Hokari et al. | 203/9 |
| 3,772,158 A * | 11/1973 | Sarno | 203/53 |
| 3,798,132 A | 3/1974 | Sarno | |
| 4,038,156 A * | 7/1977 | Knott et al. | 203/45 |
| 4,162,198 A | 7/1979 | Stockburger et al. | |
| 6,015,933 A | 1/2000 | Abrevaya et al. | |
| 2006/0235257 A1 | 10/2006 | Bridges et al. | |

FOREIGN PATENT DOCUMENTS

| | | |
|---|---|---|
| GB | 2077753 | 12/1981 |
| GB | 2077753 A * | 12/1981 |
| WO | 2005/037396 | 4/2005 |

* cited by examiner

*Primary Examiner* — Duane Smith
*Assistant Examiner* — Patrick McCarty

(57) ABSTRACT

A process for debottlenecking a system for the separation of a conjugated diolefin the system including a first extraction section having an extractive distillation column and a stripping column and a second extraction section. The process includes the steps of withdrawing a first portion of an extract from the extractive distillation column, the extract having at least the first portion and a second portion, and transferring the first portion of the extract to a flash/separation vessel; separating the first portion of the extract into a vapor phase and a liquid phase by flashing in a flash/separation vessel; and combining the liquid phase of the separated first portion of the extract with the second portion of the extract to produce an extract feed for further processing. A system and process for the separation of a conjugated diolefin from a $C_4$- or $C_5$-hydrocarbon mixture containing the conjugated diolefin and higher acetylenes are also provided.

25 Claims, 2 Drawing Sheets

US 8,080,140 B2

PROCESS FOR DEBOTTLENECKING A SYSTEM FOR THE SEPARATION OF A CONJUGATED DIOLEFIN

FIELD OF THE INVENTION

Disclosed herein is a process for the recovery of a conjugated diolefin by extractive distillation. More particularly, disclosed herein is a process for debottlenecking a system for the separation of a conjugated diolefin.

BACKGROUND OF THE INVENTION 1,3-Butadiene is a conjugated diolefin, largely used as a monomer in the production of synthetic rubber or polymerized with styrene or acrylonitrile. Smaller amounts of butadiene are used to make the solvent sulfolane, nylon via the intermediate adiponitrile, and other synthetic rubber materials such as chloroprene. Butadiene is also used in the industrial production of cyclododecatriene via a trimerization reaction.

The original commercial routes to butadiene were based on alcohol or acetylene and are no longer in use. Existing manufacturing processes all use petroleum feedstocks and are directly linked to petroleum/petrochemical operations.

In the United States, Western Europe, and Japan, butadiene is produced as a byproduct of the steam cracking process used to produce ethylene and other olefins. When mixed with steam and briefly heated to very high temperatures (often over 900° C.), aliphatic hydrocarbons give up hydrogen to produce a complex mixture of unsaturated hydrocarbons, including butadiene. The quantity of butadiene produced depends on the hydrocarbons used as feed. Light feeds, such as ethane, give primarily ethylene when cracked, but heavier feeds favor the formation of heavier olefins, butadiene, and aromatic hydrocarbons.

Typically, there are hydrocarbons in the mixture whose normal volatilities are such that separation cannot be readily achieved by ordinary fractional distillation. For example, butanes are separated with difficulty from butenes and butadiene is likewise difficultly separated from the butenes.

Conventionally, butadiene has been separated from its corresponding olefins and paraffins by an extractive distillation in the presence of a polar solvent, selected for its ability to increase the volatility of some components in the mixture relative to other components in the mixture, with the result that separation of the desired component by distillation is made possible. Polar solvents such as acetonitrile, acetone, furfural, dimethylformamide, dioxane, phenol and N-methylpyrrolidone, and their corresponding aqueous admixtures have been used in extractive distillation processes for butadiene.

Extraction of butadiene from a steam-cracker product generally offers a lower cost material than from a $C_4$ dehydrogenation plant. In conventional extractive distillation processes, the butadiene product is recovered directly from the solvent in a stripping zone at elevated temperatures. The energy required to effect the separations in the extractive distillation zone and in the stripping zone is typically supplied by a reboiler attached to each zone.

U.S. Pat. No. 3,436,436 proposes a process for fractionating a hydrocarbon mixture comprising conjugated diolefin by extractive distillation to obtain a more readily soluble hydrocarbon fraction and a less readily soluble hydrocarbon fraction. An extractive distillation column, a stripping column and a recovery column are employed. The process proposed includes the steps of passing the bottom liquid of the extractive distillation column into the recovery tower, returning the recovered gas from the recovery tower to the extractive distillation column by means of a compressor and introducing the bottom liquid of the recovery tower into the stripping column to recover the extracted materials, whereby the extractive distillation is carried out without raising the bottom temperature of the extractive distillation column, so that the diolefin and higher acetylene may be prevented from polymerization.

U.S. Pat. No. 3,436,438 proposes a process for the separation of a conjugated diolefin from a $C_4$ or $C_5$ hydrocarbon mixture containing the diolefin and higher acetylenes. According to the proposed process, the hydrocarbon mixture is subjected to extractive distillation with a solvent that comprises an N-alkyl-substituted lower aliphatic acid amide. By means of the extractive distillation, the diolefin is recovered in the form of a distillate that is substantially free from higher acetylenes. A liquid extract containing the higher acetylenes and the solvent is also recovered, the extract subjected to stripping to recover the acetylenes and the solvent.

U.S. Pat. No. 3,798,132 proposes a process for separating butadiene from mixtures of $C_4$ unsaturates that includes introducing the butadiene-containing mixture into an extractive distillation zone wherein it is distilled in the presence of a selective polar solvent, introducing the fat solvent to a first stripping zone operated at a pressure lower than that of the extractive distillation zone wherein the butadiene is stripped from the fat solvent thereby forming a butadiene-rich vapor phase, compressing the butadiene-rich vapor phase to a pressure higher than that of the extractive distillation zone, returning a portion of the compressed vapor to the bottom of the extractive distillation zone and introducing the remaining portion of the compressed vapor to a second stripping zone wherein butadiene is recovered as an overhead product.

G.B. Patent No. 2,077,753 proposes a process for the extractive distillation of hydrocarbons. The process proposed includes the steps of extractively distilling a hydrocarbon mixture in an extractive distillation apparatus using a polar extractive solvent. A first-stage extractive distillation column is operated at a higher bottom pressure than the bottom pressure of a second-stage extractive distillation column and a pre-stripping column is provided between the first-stage extractive distillation column and a first-stage stripping column and operated at a pressure equal to or lower than the bottom pressure of the first-stage extractive distillation column and equal to or higher than the bottom pressure of the second-stage extractive distillation column.

W.O. Publication No. 2005/037396 proposes a process wherein a butadiene-rich stream is transferred to a flash drum and the initial expansion causes separation of vapor from liquid, with the separated vapors flowing to a distillation column. Overhead solvent-free concentrated butadiene vapors are obtained and condensed in a water condenser and the first butadiene stream and the liquid stream flows to the stripping column to forming an overhead concentrated butadiene vapor. After compression, a second butadiene stream is obtained.

Despite these advances in the art, there is still a need for an improved process for the separation of a conjugated diolefin from a $C_4$- or $C_5$-hydrocarbon mixture.

SUMMARY OF THE INVENTION

In one aspect, a process for debottlenecking a system for the separation of a conjugated diolefin, the system including a first extraction section having an extractive distillation column and a stripping column and a second extraction section is provided. The process includes the steps of withdrawing a first portion of an extract from the extractive distillation column, the extract having at least the first portion and a second portion, and transferring the first portion of the extract to a flash/separation vessel; separating the first portion of the extract into a vapor phase and a liquid phase by flashing in a flash/separation vessel; and combining the liquid phase of the separated first portion of the extract with the second portion of the extract to produce an extract feed for further processing.

In another aspect, the process further includes the step of transferring the vapor phase of the separated first portion of the extract to a second extraction section.

In yet another aspect, the process is conducted at a flash/separation vessel temperature that is maintained below a point at which conjugated diolefin fouling occurs.

In still yet another aspect, the liquid phase of the separated first portion of the extract is transferred to the stripping tower without the assistance of a pump.

In a further aspect, the conjugated diene comprises 1,3-Butadiene.

In a yet further aspect, provided is a system for the separation of a conjugated diolefin from a $C_4$- or $C_5$-hydrocarbon mixture containing the conjugated diolefin and higher acetylenes. The system includes an extractive distillation column for subjecting the hydrocarbon mixture to extractive distillation with a polar solvent to separate a $C_4$- or $C_5$-raffinate as a distillate and to form a liquid extract containing the conjugated diolefin, the higher acetylenes and the solvent; a first conduit for withdrawing a first portion of the extract; a flash/separation vessel for receiving the first portion of the extract and separating the first portion of the extract into a vapor phase and a liquid phase; a conduit for transferring the vapor phase of the separated first portion of the extract to a second extraction section; and a stripping column for receiving the liquid phase of the separated first portion of the extract and a second portion of the extract to recover the higher acetylenes and the solvent.

In a further aspect, provided is a process for the separation of a conjugated diolefin from a $C_4$- or $C_5$-hydrocarbon mixture containing the conjugated diolefin and higher acetylenes. The process comprises the steps of subjecting the hydrocarbon mixture to extractive distillation in an extractive distillation column of a first extraction section with a polar solvent to separate a $C_4$- or $C_5$-raffinate as a distillate and to form a liquid extract containing the conjugated diolefin, the higher acetylenes and the solvent; withdrawing a first portion of the extract and transferring the first portion of the extract to a flash/separation vessel; separating the first portion of the extract into a vapor phase and a liquid phase by flashing in a flash/separation vessel; transferring the vapor phase of the separated first portion of the extract to a second extraction section; combining the liquid phase of the separated first portion of the extract with a second portion of the extract to produce an extract feed; and stripping the extract feed to recover the higher acetylenes and the solvent.

These and other features will be apparent from the detailed description taken with reference to accompanying drawings.

BRIEF DESCRIPTION OF THE DRAWINGS

The invention is further explained in the description that follows with reference to the drawing illustrating, by way of non-limiting examples, various embodiments of the invention wherein.

DETAILED DESCRIPTION OF PREFERRED EMBODIMENTS

Figure 1:
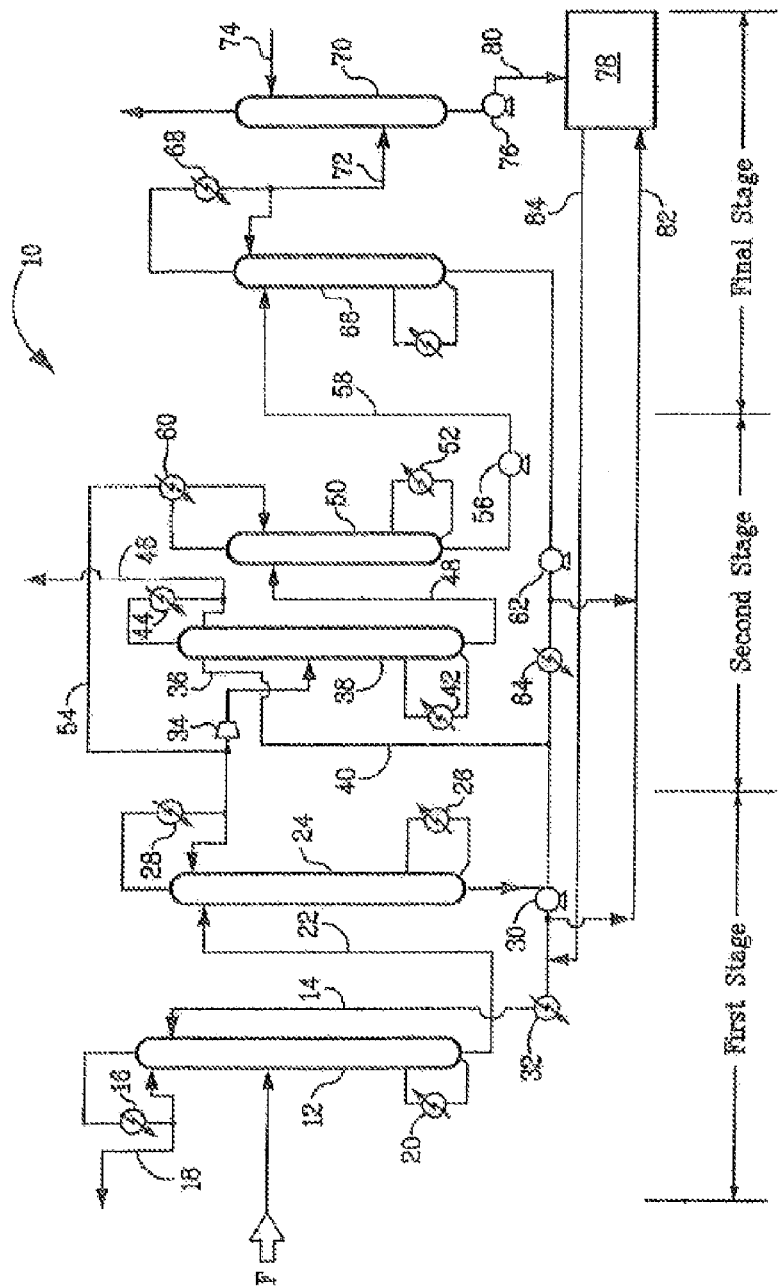
FIG. 1 presents a schematic flow diagram of a conventional system for the separation of a conjugated diolefin from a $C_4$- or $C_5$-hydrocarbon mixture containing the conjugated diolefin and higher acetylenes.
Figure 2:
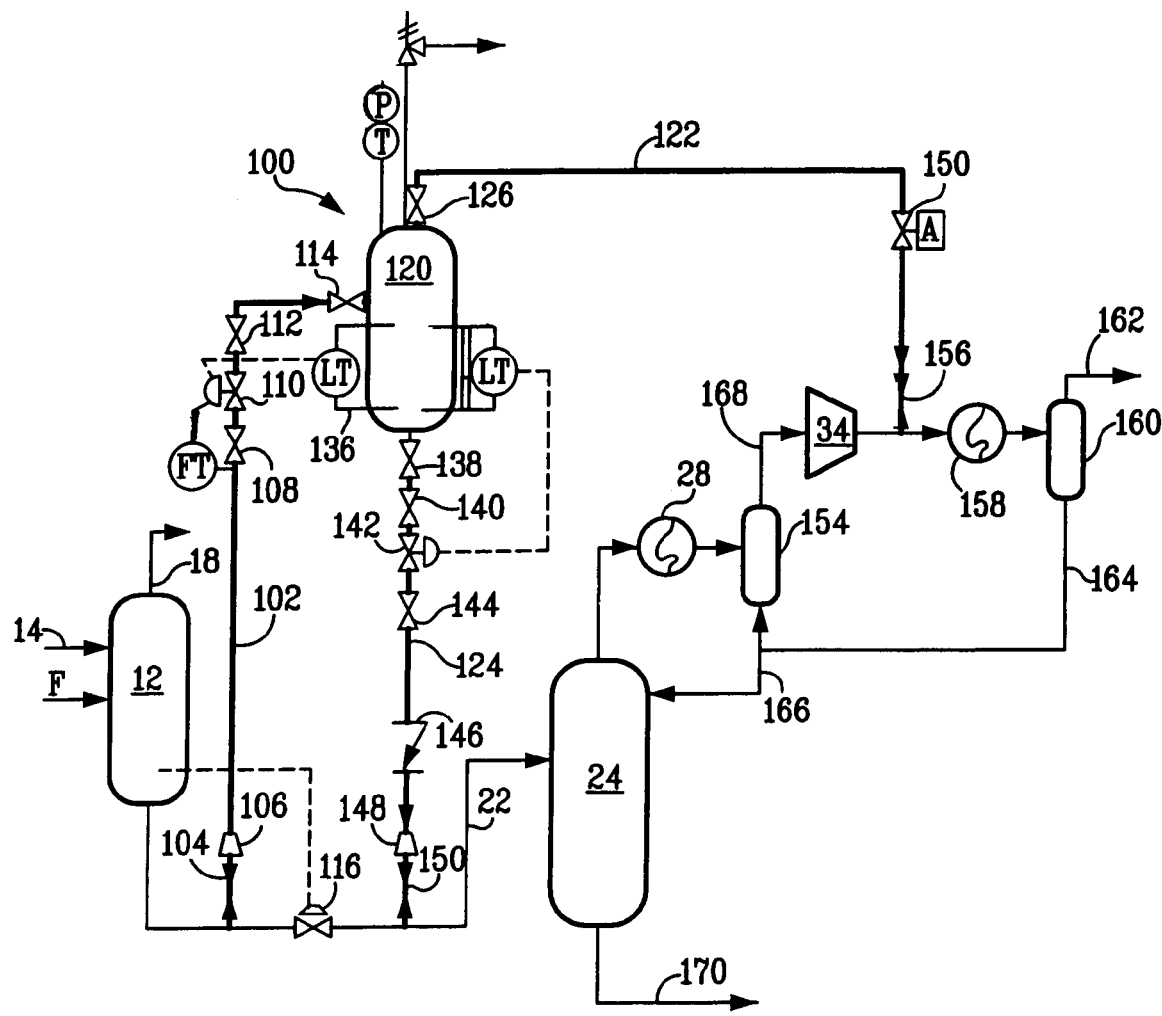
FIG. 2 presents a schematic flow diagram of a system for debottlenecking a system for the separation of a conjugated diolefin, in accordance with a form disclosed herein.

Various aspects will now be described with reference to specific forms selected for purposes of illustration. It will be appreciated that the spirit and scope of the process and system disclosed herein is not limited to the selected forms. Moreover, it is to be noted that the figures provided herein are not drawn to any particular proportion or scale, and that many variations can be made to the illustrated forms. Reference is now made to FIGS. 1-2, wherein like numerals are used to designate like parts throughout.

When an amount, concentration, or other value or parameters is given as a list of upper values and lower values, this is to be understood as specifically disclosing all ranges formed from any pair of an upper value and a lower value, regardless whether ranges are separately disclosed.

Referring now to FIG. 1, a conventional system 10 for the separation of a conjugated diolefin from a $C_4$- or $C_5$-hydrocarbon mixture containing the conjugated diolefin and higher acetylenes is shown for illustrative purposes. A conjugated diolefin-containing hydrocarbon fraction is fed into a first extractive distillation column 12 at its middle part, while a solvent is fed through a pipe 14 into first extractive distillation column 12 at an upper portion thereof. The first-stage extractive distillation is carried out in first extractive distillation column 12 by heating via reboiler 20 positioned at the bottom portion of first extractive distillation column 12. The top distillate which is in the form of vapor is condensed via a condenser 16 and a part of the resultant liquid condensate is returned back as reflux to the first extractive distillation column 12, while the remaining part which is substantially conjugated diolefin-free and mainly consists of paraffinic hydrocarbons and monoolefinic hydrocarbons is exhausted through pipe 18.

A bottom liquid comprising conjugated diolefin and higher acetylenes is withdrawn from the bottom of first extractive distillation column 12 and then passed through a pipe 22 to the top of a stripping column 24, in which stripping is conducted by heating via a reboiler 26 located at the bottom of stripping column 24. A vapor mixture of conjugated diolefin, higher acetylenes, and small amount of the used solvent is passed from the top of stripping column 24 to a cooler 28, from which a part of the resulting liquid condensate is returned back as reflux to the top of stripping column 24. From the bottom of the stripping column 24, only the solvent used is withdrawn through a pump 30 to a cooler 32. The cooled solvent is recycled through pipe 14 to the extractive distillation column 12. The vapor from the cooler 28 is passed through a compressor 34 and a pipe 36 to a second extractive distillation column 38.

Second extractive distillation column 38 may be greatly reduced in size in comparison with first extractive distillation column 12, since the hydrocarbon stock to be treated therein is free from paraffinic hydrocarbons and monoolefinic hydocarbons. As may be appreciated, the required solvent amount also may be reduced. The operation of the second extractive distillation column 38 may be the same as first extractive distillation column 12. The conjugated diolefin-containing fraction flowing through pipe 36 is fed into second extractive distillation column 38 at a mid-region thereof. The solvent is fed through a pipe 40 to the top of second extractive distillation column 38.

At the bottom of the second extractive distillation column 38, heating is effected via reboiler 42, so as to expel the dissolved conjugated diolefin. Due to its relatively low solubility, most of the conjugated diolefin is passed into a condenser 44 positioned at an upper region of second extractive distillation column 38 and then condensed. A part of the resulted liquid condensate is refluxed to second extractive distillation column 38, while the remaining part is recovered through a pipe 46 as a distillate, which is essentially conjugated diolefin free from higher acetylenes. This distillate may be subsequently subjected to ordinary distillation, if necessary. From the bottom of second extractive distillation column 38, the bottom liquid, which contains higher acetylenes having relatively high solubility together with the conjugated diolefin, are withdrawn through a pipe 48 and then reduced in pressure before the bottom liquid is passed into the upper part of the recovery tower 50, wherein the recovery of still remaining conjugated diolefin is conducted. Depending on the operating conditions of second extractive distillation column 38 and the allowance of loss in conjugated diolefin, recovery tower 50.

The bottom liquid passed into the recovery tower 50 is heated by way of a reboiler 52, wherein entrained conjugated diolefin is recovered from the top of recovery tower 50. This recovered conjugated diolefin is passed through a cooler 60 and a pipe 54 to a compressor 34 and then returned back to second extractive distillation column 38.

From the bottom of recovery tower 50, the solvent which contains higher acetylenes is withdrawn and then passed through a pump 56 and a pipe 58 to a stripping column which is similarly operated as stripping column 24 of the first stage. From the bottom, the solvent used is recovered and then returned through a pump 62, a cooler 64 and a pipe back to second extractive distillation column 38. Since this solvent is chemically the same as that used in the first stage, it may be combined with the solvent of the first stage. Vapor from the top of the column 66, which contains higher acetylenes and a small amount of conjugated diolefin, is partly refluxed by way of a cooler 68, while the remaining portion is passed to a water-washing tower 70 via pipe 72 to recover the small amount of the solvent.

In the water-washing tower 70, washing is effected by using a small amount of water fed through a pipe 74 at the top of the tower. As the solvent used is fairly soluble in water, it can be recovered completely by water-washing. The washings containing the solvent is passed through a pump 76 and a pipe 80 to a solvent purifying unit 78 wherein the solvent is purified for reuse. The solvent which is brought into recycling is contaminated with the polymer of conjugated diolefin, higher acetylenes and/or the like. Therefore, a part of the recycled solvent is withdrawn through a pipe 82 and passed into the solvent purifying unit 78 and then, after purification, is returned to a system through a pipe 84.

The production output of the system and process for the separation of a conjugated diolefin depicted in FIG. 1 tends to be limited by the first stage stripping column 24. Referring now to FIG. 2, a schematic flow diagram of a system 100 for debottlenecking a system for the separation of a conjugated diolefin 10 is presented. Also with reference to FIG. 1, in operation, a conjugated diolefin-containing hydrocarbon fraction F is fed into a first extractive distillation column 12 at its middle part, while a solvent is fed through a pipe 14 into first extractive distillation column 12 at an upper portion thereof. The first-stage extractive distillation is carried out in first extractive distillation column 12 by heating via reboiler 20, positioned at the bottom portion of first extractive distillation column 12. The top distillate, which is in the form of a vapor, is condensed via a condenser 16 and a part of the resultant liquid condensate is returned back as reflux to the first extractive distillation column 12, while the remaining part which is substantially conjugated diolefin-free and mainly consists of paraffinic hydrocarbons and monoolefinic hydrocarbons is exhausted through pipe 18.

To address the potential for process bottlenecking that occurs at the first stage stripping column 24, a first portion of a bottom extract comprising conjugated diolefin and higher acetylenes is withdrawn via a first conduit 102 through gate valve 104 and reducer 106 to gate valve 108 and pneumatic control valve 110. The first portion of the bottom extract passes through gate valves 112 and 114 and enters a flash/separation vessel 120 for receiving the first portion of the extract and separating the first portion of the extract into a vapor phase, which passes through gate valve 126 and is transferred via conduit 122. A liquid phase is withdrawn via a second conduit 124 and passes through gate valves 138 and 140 and pneumatic control valve 142. The liquid phase then passes through gate valve 144 and check valve 146 before reaching expander 148 and gate valve 150. Advantageously, the flashed liquid flows through second conduit 124 without the need of a pump. The pressure let down allows a lower flash temperature, so that fouling from butadiene is not an issue with flash/separation vessel 120.

Still referring to FIG. 2, a second portion of the bottom extract of first extractive distillation column 12 passes through pipe 22 and flows through pneumatic control valve 116. Thereafter, the liquid phase of the separated first portion of the extract withdrawn from flash/separation vessel 120 via a second conduit 124 is combined with the second portion of the bottom extract transferred via pipe 22 to produce an extract feed for further processing. The extract feed is transferred through the remainder of pipe 22, wherein it is introduced into stripping column 24 to recover the higher acetylenes and the solvent.

Referring also to FIG. 1, stripping is conducted by heating via a reboiler 26 located at the bottom of stripping column 24. A vapor mixture of conjugated diolefin, higher acetylenes, and small amount of the used solvent is passed from the top of stripping column 24 to a cooler 28, from which a part of the resulting liquid condensate is returned back as reflux to the top of stripping column 24. From the bottom of the stripping column 24, only the solvent used is withdrawn through conduit 170 via a pump 30 to a cooler 32. The cooled solvent is recycled through pipe 14 to the extractive distillation column 12. The vapor from the cooler 28 is passed through a compressor 34 and a pipe 36 to a second extractive distillation column 38.

As shown in FIG. 2, the vapor phase of the separated first portion of the bottom extract is transferred via conduit 122, gate valves 150 and 156 to a point downstream of a first stage compressor 34 and upstream of discharge cooler 158 where it passes to separator 160, with an overhead portion passing through conduit 162 to the second stage extraction section (see FIG. 1). In the form depicted in FIG. 2, the bottoms from separator 160 pass through conduit 164, where a portion is transferred to separator 154, through conduit 168 and is returned to first stage compressor 34, while a portion is returned to stripping column 24 via conduit 166. As shown, an overhead from stripping column 24 is withdrawn via conduit 154 and passes through cooler 28 before entering separator 154.

In another form, a process for the separation of a conjugated diolefin from a $C_4$- or $C_5$-hydrocarbon mixture containing the conjugated diolefin and higher acetylenes is provided. The process includes the steps of subjecting the hydrocarbon mixture F to extractive distillation in an extractive distillation column 12 of a first extraction section with a polar solvent to separate a $C_4$- or $C_5$-raffinate as a distillate and to form a liquid extract containing the conjugated diolefin, the higher acetylenes and the solvent, withdrawing a first portion of the extract and transferring the first portion of the extract to a flash/separation vessel 120, separating the first portion of the extract into a vapor phase and a liquid phase by flashing in a flash/separation vessel 120 transferring the vapor phase of the separated first portion of the extract to a second extraction section, combining the liquid phase of the separated first portion of the extract with a second portion of the extract to produce an extract feed and stripping the extract feed to recover the higher acetylenes and the solvent.

In operation, the amount of the first portion of the extract to be withdrawn and transferred to flash/separation vessel 120 is less than about 95% of the total volume of extract produced by extractive distillation column 12 and at least about 5% of the total volume of extract produced by extractive distillation column 12, or at least about 10% of the total volume of extract produced by extractive distillation column 12, or at least about 15% of the total volume of extract produced by extractive distillation column 12, or at least about 20% of the total volume of extract produced by extractive distillation column 12 or at least 25% or more of the total volume of extract produced by extractive distillation column 12. The amount of the second portion of the extract for subsequent combination with the liquid phase of the separated first portion of the extract is less than about 95% of the total volume of extract produced by extractive distillation column 12 and at least about 50% of the total volume of extract produced by extractive distillation column 12, or at least about 75% of the total volume of extract produced by extractive distillation column 12, or at least about 80% of the total volume of extract produced by extractive distillation column 12, or at least about 85% of the total volume of extract produced by extractive distillation column 12 or at least 90% or more of the total volume of extract produced by extractive distillation column 12.

To increase the production of conjugated diolefins from a $C_4$- or $C_5$-hydrocarbon mixture containing the conjugated diolefins and higher acetylenes, in one commercial plant design, a flash separation vessel having a volume of about 20 ft$^3$ can handle a first extract portion volume of about 15% of the total volume of extract produced by the plant's extractive distillation column. In this particular plant, a first extract portion volume of about 6% of the total volume of extract produced by the plant's extractive distillation column can yield an increase in the production of conjugated diolefins of about 50 klb/day.

Higher acetylenes, that is, acetylenically unsaturated hydrocarbons and/or allenically unsaturated hydrocarbons, can be removed from the conjugated diolefin-containing hydrocarbon fraction by subjecting the fraction to extractive distillation with an N-alkyl-substituted lower aliphatic acid amide to obtain the higher acetylenes as the extracted fraction. Highly pure conjugated diolefins can be recovered from the conjugated diolefin-containing hydrocarbon mixture by carrying out the extractive distillation with an N-alkyl-substituted lower aliphatic acid amide to obtain a fraction mainly comprising the conjugated diolefins and then further subjecting the fraction to extractive distillation with the same solvent as in the first step to remove acetylenically and/or allenically unsaturated hydrocarbons as the extract. An optional ordinary distillation may be added for further purification, if desired.

Suitable N-alkyl-substituted lower aliphatic acid amides are represented by the following general formula:

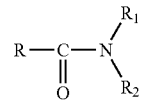

wherein R and $R_1$ individually can be a hydrogen atom or a lower alkyl radical having 1 to 3 carbon atoms, such as methyl, ethyl, propyl and isopropyl; and $R_2$ can be a lower alkyl radical having 1 to 3 carbon atoms, such as methyl, ethyl, propyl and isopropyl. Typical N-alkyl-substituted lower aliphatic acid amides include N-monoalkyl-or N,N-dialkyl-substituted derivatives of formamide, acetamide, propionamide and butyramide. Specifically, they include monomethyl formamide, dimethyl formamide, diethyl formamide, dimethyl acetamide, methylpropyl acetamide, dimethyl propionamide, monoethyl butyramide, etc. Among these, dimethyl formamide, diethyl formamide and dimethyl acetamide may be selected because of their extracting power, boiling point and availability. N-alkyl-substituted lower aliphatic acid amides of the above formula that have an R, $R_1$ and $R_2$ of more than three carbon atoms yield poor results due to their poor extracting power and high boiling point.

As may be apparent to those skilled in the art, an N-alkyl-substituted lower aliphatic acid amide used as a solvent herein may be added with any other suitable additive to facilitate extractive distillation. For example, a polymerization inhibitor may be used since the polymerization of unsaturated components occasionally takes place under operating conditions which chokes the distillation apparatus employed. Water, methanol or any other suitable additive having a boiling point higher than that of the material to be extracted, but lower than the used N-alkyl-substituted aliphatic acid amide can be used together with the solvent, permitting extractive distillation to be conducted at a lower operating temperature.

In the separation of conjugated diolefins by extractive distillation, it is common to use as a solvent a mixture of a polar substance with a small amount of water, in order to decrease operating temperature, to improve selectivity and to prevent polymer formation. However, use of water or methanol in combination with an N-alkyl-substituted aliphatic acid amide is not always desirable, as this sometimes causes corrosion and a decrease of solubility of individual solvents. As a polymerization inhibitor to be added to the solvent, those which can prevent polymerization of conjugated diolefins and higher acetylenes and those that can take chain transfer action may be used. For example, tertiary-butyl catechol, sulfur, sodium nitrite, furfural, benzaldehyde and aromatic nitro-compounds are suitable polymerization inhibitors. Among these, furfural, benzaldehyde and aromatic nitro compounds, singley or in combination, may be used. These additives should be used in amount of less than 30% by weight, so that the efficient action of an N-alkyl-substituted aliphatic acid amide may be ensured. If the additive is a polymerization inhibitor, an amount of about 0.01 to 30% by weight based on the solvent will be satisfactory. About 0.1 to 10% by weight of such inhibitor is preferable.

Sometimes, a flooding phenomenon is observed in the extractive distillation column owing to the formation of polymeric material from the unsaturated hydrocarbons and/or additives. In such a case, a small amount of antifoaming agent such as polydimethylsiloxane may be used.

A suitable conjugated diolefin-containing hydrocarbon mixture feedstock may be a $C_4$- or $C_5$-fraction obtained by thermal cracking of a petroleum fraction, such as LPG, naphtha, etc. Additionally, a butadiene-containing fraction obtained by dehydrogenation of n-butane and/or n-butene, and an isoprene-containing fraction obtained by dehydrogenation of isopentane and/or isoamylene may be used.

The process disclosed herein can be coupled with various steps for the extraction of conjugated diolefins. In the case of extraction, saturated hydrocarbons and monoolefins are removed by extractive distillation with acetonitrile, N-methyl pyrrolidone or the like to obtain a fraction mainly comprising 1,3-butadiene, which fraction is then subjected to an extractive distillation process of the type disclosed herein, to remove entrained higher acetylenes, such as ethyl acetylene, vinyl acetylene, 1,2-butadiene, etc. Alternatively, the $C_4$-fraction may subjected to extractive distillation in accordance herewith to remove higher acetylenes as an extracted portion, with the distilled portion treated by conventionally known procedures to obtain 1,3-butadiene. The former form is more convenient than the latter, since the gas volume to be treated in the former form is less than that in the latter and accordingly the apparatus required in the former is more compact than that of the latter. Further, if a solvent mainly comprising an N-alkyl-substituted lower aliphatic acid amide is used in the first extractive distillation stage of the above-mentioned former form, it is possible to obtain 1,3-butadiene sufficiently pure to prepare stereospecific polybutadiene, while common solvent-supplying and solvent-recovering equipment is used with an economical advantage.

When a hydrocarbon mixture containing paraffinic hydrocarbons, monoolefinic hydrocarbons, conjugated diolefins and higher acetylenes is subjected to extractive distillation with a solvent mainly comprising an N-alkyl-substituted lower aliphatic acid amide, the paraffinic hydrocarbons and monoolefinic hydrocarbons are recovered as a top distillate of the extractive distillation column, while the conjugated diolefins and higher acetylenes recovered as an extract. The extracted hydrocarbon fraction is further subjected to extractive distillation with the same solvent as described hereinabove, whereby pure conjugated diolefins are recovered as a top distillate while the higher acetylenes recovered as an extract. Thus, the two-stage extractive distillation process can be carried out to recover the conjugated diolefins.

If a hydrocarbon mixture containing, together with a desirable conjugated diolefin, hydrocarbons which are less soluble than the conjugated diolefin and those which are more soluble than the conjugated diolefin is subjected to the first-stage extractive distillation, a mixture of the conjugated diolefin and the more soluble hydrocarbons is obtained as an extract, while the less soluble hydrocarbons are removed as a top distillate. Then the extract of the first stage is subjected to the second-stage extractive distillation whereby the conjugated diolefin is recovered as a top distillate while the more soluble hydrocarbons are removed as an extract.

For example, the extractive distillation of a $C_4$-fraction yields 1,3-butadiene, ethyl acetylene, vinyl acetylene and 1,2-butadiene as the extract, which, when subjected to further extractive distillation, produces 1,3-butadiene as a top distillate while ethyl acetylene, vinyl acetylene, 1,2-butadiene or other higher acetylenes are yielded as an extract. Extractive distillation of a $C_5$-fraction is somewhat more complicated than that of the $C_4$-fraction because of the existence of other additional conjugated diolefins than the desired conjugated diolefin. In the case of the $C_5$-fraction, however, the desired conjugated diolefin is obtained by two-stage extractive distillation. For example, if isoprene is desired, the extractive distillation of a $C_5$-fraction yields isoprene, cyclopentadiene, 1,3-pentadiene, propyl acetylene, cyclopentene and other higher acetylenes as an extract, which, when subjected to further extractive distillation, yields isoprene as a top distillate, while cyclopentadiene, 1,3-pentadiene, propyl acetylene, cyclopentene and other higher acetylenes are contained in a bottom liquid.

As may be appreciated by those skilled in the art, hydrocarbons having different carbon atoms from that of the desired conjugated diolefin are present in small amounts in the $C_4$- or $C_5$-fraction. Some of these hydrocarbons occasionally remain in the conjugated diolefin fraction obtained by the extractive distillation process. In such a case, a subsequent ordinary distillation process to the extractive distillation process may be used to remove these hydrocarbons effectively. Also, the subsequent distillation removes the impurities having the same carbon atoms as the desired conjugated diolefin, when the boiling point of the impurities is fairly different from that of the diolefin.

As also may be appreciated by those skilled in the art, it is not economical to completely separate methylacetylene ($C_3$-hydrocarbon) or isopentane ($C_5$-hydrocarbon) from 1,3-butadiene fraction containing a small amount of methyl acetylene or isopentane, by extractive distillation. A subsequent ordinary distillation can easily remove these impurities from crude 1,3-butadiene. A small amount of remaining ethyl acetylene and/or 1,2-butadiene may also be removed. But vinyl acetylene must be completely removed by the extractive distillation, since vinyl acetylene forms with cis- and/or trans-butene, an azeotropic mixture that has a close boiling point close to that of 1,3-butadiene. Similarly, in the case of a $C_5$-fraction, the subsequent ordinary distillation may be used to obtain a pure conjugated diolefin, which is desired due to the existence of many components of $C_5$-fraction and the contamination of $C_4$- or $C_6$-hydrocarbons.

Acetylenically unsaturated hydrocarbons include those compounds which have at least one carbon-to-carbon triple bond, e.g. ethyl acetylene, dimethyl acetylene, vinyl acetylene, di-acetylene, propyl acetylene, allyl acetyene, etc. Allenically unsaturated hydrocarbons include those compounds which have a cumulated carbon-to-carbon double bond, e.g. 1,2-butadiene, 1,2-pentadiene, etc. In practice, it is possible to remove these acetylenically unsaturated and allenically unsaturated hydrocarbons from a conjugated diolefin-containing fraction, thereby leaving highly pure conjugated diolefin as is desired for the production of stereospecific polymeric diolefin.

As may be appreciated, the process for debottlenecking a system for the separation of a conjugated diolefin disclosed herein is simple, requiring only small changes to existing operations. Moreover, no preheater is required in this otherwise high fouling service, with the temperature in the flash/separation vessel maintained below the fouling temperature of 270° F. Since the process requires only a slip stream portion of the bottom extract of the extraction distillation tower to be processed within the flash/separation vessel, rather than the entire stream, the investment in the new facility is low. The workable pressure range within the flash/separation vessel is relatively wide, so there is no need to use a pump to push the flashed liquid back to the stripper tower feed. Additionally, energy savings may be realized with respect to stripper tower steam, since, instead of using additional heat, pressure letdown is used to flash off vapor in the flash/separation vessel.

As may be appreciated, the system disclosed herein may be retrofitted to a wide variety of butadiene recovery units. The process of treating a slip stream and by-passing a portion of the feed to a congested process tower could be applied to other processes, as well.

EXAMPLE

To demonstrate the effectiveness of the system and process disclosed herein, a process simulation was conducted. Process simulation tool, PRO/II Version 7.1, available from the SimSci-Esscor unit of Invensys Process Systems of Lake Forest, Calif. was utilized together with the ExxonMobil engineering design and layout (EDL) package to simulate the process and design disclosed herein. The ExxonMobil tray rating tool was used to simulate a stripper tower. The simulation was validated with tower flood test data and confirmed with tower Gamma scans.

For a project design of interest, to increase the butadiene production by 50 klb/day, the size of the flash/separation vessel is 3 feet by 7 feet. The capital investment was estimated to be $880,000 and the production credit was estimated to be $1,200,000/year. Energy savings were estimated to be about $78,000/year.

The table below presents the corresponding design parameters of the simulation described above.

TABLE

|  | Normal Rate | Design Rate |
| --- | --- | --- |
| % Slip Stream from Extraction Distillation Tower Bottoms | 8% | 15% |
| Inlet to Flash/Separation Vessel (klb/hr) | 42.5 | 103.0 |
| Vapor (klb/hr) | 2.7 | 6.6 |
| Liquid (klb/hr) | 39.8 | 96.4 |

All patents, test procedures, and other documents cited herein, including priority documents, are fully incorporated by reference to the extent such disclosure is not inconsistent with this invention and for all jurisdictions in which such incorporation is permitted.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein, but rather that the claims be construed as encompassing all the features of patentable novelty which reside in the invention, including all features which would be treated as equivalents thereof by those skilled in the art to which the invention pertains.

What is claimed is:

1. A process for debottlenecking a system for the separation of a conjugated diolefin, said system comprising a first extraction section comprising an extractive distillation column and a stripping column and a second extraction section, said process comprising the steps of:
   (a) withdrawing a first portion of an extract from the extractive distillation column, the extract having at least the first portion and a second portion, and transferring the first portion of the extract to a flash/separation vessel;
   (b) separating the first portion of the extract into a vapor phase and a liquid phase by flashing in a flash/separation vessel; and
   (c) combining the liquid phase of the separated first portion of the extract with the second portion of the extract to produce an extract feed for further processing.

2. The process of claim 1, further comprising the step of stripping the extract feed of step (c).

3. The process of claim 2, wherein said stripping step is conducted in the absence of a hydrocarbon diluent.

4. The process of claim 1, further comprising the step of transferring the vapor phase of the separated first portion of the extract to a second extraction section.

5. The process of claim 1, wherein the liquid phase of the separated first portion of the extract is combined with the second portion of the extract in the stripping tower.

6. The process of claim 1, wherein the temperature of the flash/separation vessel is maintained below a point at which conjugated diolefin fouling occurs.

7. The process of claim 6, wherein the temperature of the flash/separation vessel is maintained below about 270° F.

8. The process of claim 1, wherein the vapor phase of the separated first portion of the extract is transferred to a point downstream of a first stage compressor and upstream of a discharge cooler to the second extraction section.

9. The process of claim 1, wherein the conjugated diolefin comprises 1, 3-Butadiene.

10. The process of claim 1, wherein extractive distillation is performed under anhydrous conditions.

11. The process of claim 1, wherein the liquid phase of the separated first portion of the extract is transferred to the stripping tower without the assistance of a pump.

12. The process of claim 1, wherein the amount of the first portion of the extract to be withdrawn and transferred to the flash/separation vessel is between about 5% and about 95% of the total volume of extract produced by the extractive distillation column.

13. The process of claim 12, wherein the amount of the first portion of the extract to be withdrawn and transferred to the flash/separation vessel is between about 10% and about 95% of the total volume of extract produced by the extractive distillation column.

14. The process of claim 12, wherein the amount of the first portion of the extract to be withdrawn and transferred to the flash/separation vessel is between about 15% and about 95% of the total volume of extract produced by the extractive distillation column.

15. A process for the separation of a conjugated diolefin from a $C_4$- or $C_5$-hydrocarbon mixture containing the conjugated diolefin and higher acetylenes, the process comprising the steps of:
   (a) subjecting the hydrocarbon mixture to extractive distillation in an extractive distillation column of a first extraction section with a polar solvent to separate a $C_4$- or $C_5$-raffinate as a distillate and to form a liquid extract containing the conjugated diolefin, the higher acetylenes and the solvent;
   (b) withdrawing a first portion of the extract and transferring the first portion of the extract to a flash/separation vessel;
   (c) separating the first portion of the extract into a vapor phase and a liquid phase by flashing in a flash/separation vessel;
   (d) transferring the vapor phase of the separated first portion of the extract to a second extraction section;
   (e) combining the liquid phase of the separated first portion of the extract with a second portion of the extract to produce an extract feed; and
   (f) stripping the extract feed of step (e) to recover the higher acetylenes and the solvent.

16. The process of claim 15, wherein the temperature of the flash/separation vessel is maintained below a point at which conjugated diolefin fouling occurs.

17. The process of claim 16, wherein the temperature of the flash/separation vessel is maintained below about 270° F.

18. The process of claim 15, wherein the vapor phase of the separated first portion of the extract is transferred to a point downstream of a first stage compressor and upstream of a discharge cooler to a second extraction section.

19. The process of claim 15, wherein the conjugated diolefin comprises 1,3-Butadiene.

20. The process of claim 15, wherein the polar solvent comprises an N-alkyl-substituted lower aliphatic acid amide.

21. The process of claim 20, wherein the solvent is dimethyl formamide, diethyl formamide or dimethyl acetamide.

22. The process of claim 21, wherein the solvent is used in admixture with from about 0.01 to 30% by weight of a polymerization inhibitor.

23. The process of claim 15, wherein the extractive distillation is performed under anhydrous conditions.

24. The process of claim 15, wherein the liquid phase of the separated first portion of the extract is transferred to the stripping tower without the assistance of a pump.

25. The process of claim 15, wherein said stripping step is conducted in the absence of a hydrocarbon diluent.

\* \* \* \* \*